(12) United States Patent
Hung et al.

(10) Patent No.: US 11,020,446 B2
(45) Date of Patent: Jun. 1, 2021

(54) METHOD FOR PREPARING TEA LEAF EXTRACT

(71) Applicant: GREENEPIC BIOTECH CORPORATION, Yunlin County (TW)

(72) Inventors: Yung-Han Hung, Yunlin County (TW); Pin-Wen Chen, Yunlin County (TW); Yu-Tsai Chen, Yunlin County (TW)

(73) Assignee: GREENEPIC BIOTECH CORPORATION, Yunlin County (TW)

( * ) Notice: Subject to any disclaimer, the term of this patent is extended or adjusted under 35 U.S.C. 154(b) by 204 days.

(21) Appl. No.: 16/133,760

(22) Filed: Sep. 18, 2018

(65) Prior Publication Data

US 2019/0224265 A1  Jul. 25, 2019

(30) Foreign Application Priority Data

Jan. 24, 2018 (TW) ................. 107102562

(51) Int. Cl.
*A61K 36/82* (2006.01)
*A61K 36/00* (2006.01)

(52) U.S. Cl.
CPC .......... *A61K 36/82* (2013.01); *A61K 2236/33* (2013.01)

(58) Field of Classification Search
None
See application file for complete search history.

(56) References Cited

U.S. PATENT DOCUMENTS

| 2009/0001002 A1* | 1/2009 | Bauer | C02F 3/327 210/138 |
| 2011/0052557 A1* | 3/2011 | Huang | A61P 17/02 424/94.4 |
| 2011/0217420 A1* | 9/2011 | Lerner | A23F 5/46 426/78 |

FOREIGN PATENT DOCUMENTS

| CN | 1803599 A | 7/2006 |
| CN | 101225082 A | 7/2008 |
| CN | 101837948 A | 9/2010 |
| CN | 102020272 A | 4/2011 |
| CN | 102552546 A | 7/2012 |

* cited by examiner

*Primary Examiner* — Michael Barker
*Assistant Examiner* — Randall O Winston
(74) *Attorney, Agent, or Firm* — WPAT, PC

(57) ABSTRACT

A method for preparing a tea leaf extract is used for preparing the tea leaf extract with improved anti-oxidation activity. The method includes smoldering a rice husk sample at 200-400° C. in a low oxygen environment for 2-4 hours, followed by burning at 400-600° C. in an atmospheric environment for 2-4 hours to obtain a rice husk silica. An oxygen concentration in the low oxygen environment is below 5%. The rice husk silica is dissolved in an alkaline solution to obtain a rice husk silica solution. A tea leaf sample is then extracted by the rice husk silica solution.

8 Claims, No Drawings

METHOD FOR PREPARING TEA LEAF EXTRACT

CROSS REFERENCE TO RELATED APPLICATIONS

The application claims the benefit of Taiwan application serial No. 107102562, filed Jan. 24, 2018, the entire contents of which are incorporated herein by reference.

BACKGROUND OF THE INVENTION

1. Field of the Invention

The present invention generally relates to a method for preparing a tea leaf extract and, more particularly, to a method for preparing the tea leaf extract with great anti-oxidation activity.

2. Description of the Related Art

Tea leaf having various active substances with anti-oxidation activity, such as (+)-catechin, epicatechin (EC), epigallocatechin (EGC), epicatechin gallate (ECG) and epigallocatechin gallate (EGCG), is considered to be benefit to healthy.

The tea leaf is generally soaked in hot water, and active substances with anti-oxidation activity in the tea leaf can be released and dissolved in the water to form tea. Customers can absorb the active substances with anti-oxidation activity by drinking tea. Moreover, taking a tea leaf extract with improved anti-oxidation activity, which is prepared by a specific extraction process, can be the way to effectively improve health of the customers.

In light of this, it is necessary to provide a method for preparing a tea leaf extract.

SUMMARY OF THE INVENTION

It is therefore an objective of the present invention to provide a method for preparing a tea leaf extract with improved anti-oxidation activity.

One embodiment of the present invention discloses a method for preparing a tea leaf extract. The method includes smoldering a rice husk sample at 200-400° C. in a low oxygen environment for 2-4 hours, followed by burning at 400-600° C. in a low oxygen environment in an atmospheric environment for 2-4 hours to obtain a rice husk silica. An oxygen level in the low oxygen environment is below 5%. The rice husk silica is dissolved in an alkaline solution to obtain a rice husk silica solution. A tea leaf sample is extracted by the rice husk silica solution to obtain the tea leaf extract. As an example, the rich husk sample is smoldered at 300° C. for 2 hours, and is burned at 400-600° C. for 2 hours to obtain the rice husk silica. Accordingly, by the use of the rich husk silica solution, the active substances with anti-oxidation activity in the tea leaf sample can be easily released and dissolved in the rice husk silica solution. Therefore, the tea leaf extract prepared by the method for preparing the tea leaf extract according the present invention has improved anti-oxidation activity.

In an example, the tea leaf sample is extracted at 4-30° C. for 4-6 hours. As an example, the tea leaf sample is extracted at 25° C. for 4 hours. As such, by the adjustment of temperature, as well as time, for extraction, the prepared tea leaf extract has preferable anti-oxidation activity.

In an example, before the tea leaf sample is extracted by the rice husk silica solution, the tea leaf sample is soaked in the rice husk silica solution. As an example, 100 grams of the tea leaf sample is soaked in 500 mL of the rice husk silica solution. As such, the active substances with anti-oxidation activity in the tea leaf sample can be effectively released and dissolved in the rice husk silica solution.

In an example, the alkaline solution is selected from an aqueous sodium hydroxide solution, an aqueous potassium hydroxide solution or an aqueous sodium carbonate solution. As such, by the use of the specific alkaline solution, the rice husk silica solution can be effectively formed, and can be used as the extractant.

In an example, before the rich husk sample is smoldered in the low oxygen environment, the rice husk sample is soaked in a lignin decomposer, followed by drying. As an example, the lignin decomposer is selected from an aqueous hydrochloric acid solution, an aqueous acetic acid solution, an aqueous nitric acid solution, an aqueous formic acid solution or an aqueous sodium hypochlorite solution. Preferably, the rice husk sample can be soaked in the aqueous sodium hypochlorite solution (2%) for 2 hours. As such, by the decomposition of lignin in the rice husk sample, the rice husk silica solution with a more purified $SiO_2$ can be obtained, improving the following extraction efficacy.

DETAILED DESCRIPTION OF THE INVENTION

In a method for preparing a tea leaf extract according to an embodiment of the present invention, a rice husk silica solution (rice husk silica liquid, RHSL) is used to extract a tea leaf sample. With such performance, active substances in the tea leaf sample can be released and dissolved in the rich husk silica solution, and the tea leaf extract can be thus obtained.

Specifically, the rice husk silica solution includes a rice husk derived amorphous $SiO_2$. Moreover, the rice husk silica solution is obtained by a method including a smoldering step, a burning step and a dissolving step. In the smolder step, a rich husk sample is smoldered at 200-400° C. for 2-4 hours in a low oxygen environment where the oxygen concentration is below 5%. In the burning step, the smoldered product is burned at 400-600° C. for 2-4 hours in an atmospheric environment where the oxygen concentration is about 20% to obtain a rice husk silica. In the following dissolving step, the rice husk silica is dissolved in an alkaline solution to obtain the rice husk silica solution.

The rice husk sample, the coatings of rice, is an agricultural byproduct and is removed from the raw grain to reveal whole brown rice including bran, aleurone layer and germ. The rice husk sample can be first soaked in a lignin decomposer, such as an aqueous hydrochloric acid solution ($HCl_{(aq)}$), an aqueous acetic acid solution ($AcOH_{(aq)}$), an aqueous nitric acid solution, an aqueous formic acid solution or an aqueous sodium hypochlorite solution ($NaClO_{(aq)}$). After lignin in the rice husk sample is decomposed by the lignin decomposer, the rice husk sample is washed and dried. The dried rich husk sample can then be placed in an air closed system for performing the smoldering step and the burning step. As such, the husk silica solution with a more purified $SiO_2$ can be obtained, improving the following extraction efficacy. In this embodiment, the rice husk sample is soaked in the aqueous sodium hypochlorite solution (2%) for 2 hours.

After the smoldering step and the burning step in the air closed system, the rice husk silica in white color can be obtained. In this embodiment, the smoldering step is carried out at 300° C. for 2 hours, and the burning step is carried out at 400-600° C. for 2 hours.

In the dissolving step, the rice husk silica can be dissolved in the alkaline solution to obtain the rice husk silica solution which can be used as an extractant. As an example, the alkaline solution can be an aqueous sodium hydroxide solution ($NaOH_{(aq)}$), an aqueous potassium hydroxide solution ($KOH_{(aq)}$), or aqueous sodium carbonate solution ($Na_2CO_{3(aq)}$). In this embodiment, 100 grams of the rice husk silica is dissolved in 1 liter of the alkaline solution (2-5%).

The rice husk silica solution can then be applied to extract the tea leaf sample. The tea leaf sample can be Sunlinksea high mountain tea (hand harvested Sunlinksea high mountain tea, purchased from Xingcha House, DFF-teagift12). The tea leaf sample can be soaked in the rice husk silica solution, followed by being extracted at 4-30° C. for 4-6 hours. In this example, 100 grams of the tea leaf sample is soaked in 500 milliliters of the rice husk silica solution, and is extracted at 25° C. for 4 hours. Therefore, active substances in the tea leaf sample can be released and dissolved in the rice husk silica solution, obtaining a crude extract. The crude extract can be further concentrated by concentration under reduced pressure and drying to obtain the tea leaf extract.

To validate the tea leaf extract with improved anti-oxidation activity can be prepared by the method for preparing the tea leaf extract according to the present invention, water (group A0), the aqueous sodium hydroxide solution (group A1, 5%), edible $SiO_2$ (group A2, dissolved in the aqueous sodium hydroxide solution) and the rice husk silica solution (group A3, dissolved in the aqueous sodium hydroxide solution) are used as the extractant to extract the tea leaf sample, respectively. DPPH clearance ability and ABTS clearance ability of the obtained tea leaf extract of groups A0-A3 are measured, respectively, as shown in TABLE 1.

TABLE 1

| Group | $IC_{50}$ (μg/mL) | |
|---|---|---|
| | DPPH | ABTS |
| A0 | 229.0 | 41.36 |
| A1 | 317.8 | 44.92 |
| A2 | 214.2 | 66.84 |
| A3 | 123.0 | 22.75 |

Referring to TABLE 1, compared to the tea leaf extracts of groups A0-A2, the tea leaf extract of group A3 shows a significant lower $IC_{50}$ in both DPPH and ABTS. That is, the tea leaf extract obtained by extracting the tea leaf sample by the rice husk silica solution (group A3) has improved anti-oxidation activity, compared to the tea leaf extracts of groups A0-A2.

Accordingly, by the use of the rice husk silica solution, the active substances with anti-oxidation activity in the tea leaf sample can be easily released and dissolved in the rich husk silica solution. Therefore, the tea leaf extract prepared by the method for preparing the tea leaf extract according to the present invention has improved anti-oxidation activity.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for preparing a tea leaf extract, comprising:
   obtaining a smoldered rice husk sample by smoldering a rice husk sample at 200-400° C. in an environment with an oxygen level below 5% for 2-4 hours;
   obtaining a rice husk silica by burning the smoldered rice husk sample at 400-600° C. for 2-4 hours;
   obtaining a rice husk silica solution by dissolving the rice husk silica in an alkaline solution; and
   obtaining the tea leaf extract by soaking a tea leaf sample in the rice husk silica solution at 4-30° C. for 4-6 hours.

2. The method for preparing the tea leaf extract as claimed in claim 1, wherein the tea leaf sample is soaked in the rice husk silica solution at 25° C. for 4 hours.

3. The method for preparing the tea leaf extract as claimed in claim 1, wherein 100-gram of the tea leaf sample is soaked in 500 mL of the rice husk silica solution.

4. The method for preparing the tea leaf extract as claimed in claim 1, wherein the rice husk sample is smoldered at 300° C. for 2 hours, and the smoldered rice husk sample is burned at 400-600° C. for 2 hours.

5. The method for preparing the tea leaf extract as claimed in claim 1, wherein the alkaline solution is an aqueous sodium hydroxide solution, an aqueous potassium hydroxide solution, or an aqueous sodium carbonate solution.

6. The method for preparing the tea leaf extract as claimed in claim 1, wherein the rice husk sample is soaked in a lignin decomposer and then dried before being smoldered.

7. The method for preparing the tea leaf extract as claimed in claim 6, wherein the lignin decomposer is an aqueous hydrochloric acid solution, an aqueous acetic acid solution, an aqueous nitric acid solution, an aqueous formic acid solution or an aqueous sodium hypochlorite solution.

8. The method for preparing the tea leaf extract as claimed in claim 7, wherein the rice husk sample is soaked in the aqueous sodium hypochlorite solution with a 2% concentration of sodium hypochlorite for 2 hours.

* * * * *